ns Patent [19] [11] 4,044,057
Bloomfield et al. [45] Aug. 23, 1977

[54] AROMA CHEMICALS

[75] Inventors: Jordan J. Bloomfield; Dennis C. Owsley, both of St. Louis, Mo.

[73] Assignee: Monsanto Company, St. Louis, Mo.

[21] Appl. No.: 645,182

[22] Filed: Dec. 29, 1975

[51] Int. Cl.$^2$ .............................................. C07C 35/22
[52] U.S. Cl. ................................ 260/617 F; 252/522; 252/89 R; 260/586 F; 424/59; 424/65; 424/69; 424/70; 424/71; 424/76; 424/365
[58] Field of Search ............ 260/617 F, 631 R, 586 F

[56] References Cited

U.S. PATENT DOCUMENTS 2,912,462  11/1959  Goldstein et al. ............... 260/617 F

OTHER PUBLICATIONS

Casals et al., Tetrahedron Letters, No. 17, pp. 1647-1650 (1972).
Singh, J. Org. Chem., vol. 36 (22), pp. 3334-3339 (1971).

Primary Examiner—James O. Thomas, Jr.
Assistant Examiner—James H. Reamer
Attorney, Agent, or Firm—H. C. Stanley

[57] ABSTRACT

Compounds represented by the structural formulae

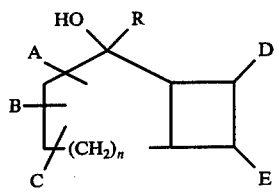
(I)

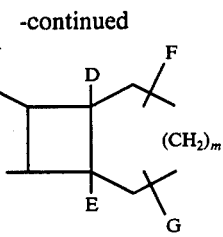

(II)

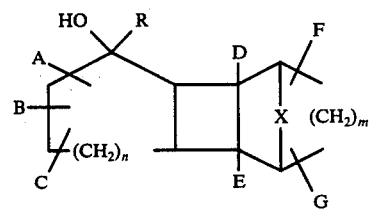

(III)

wherein $n$ is an integer 0 or 1; A, B and C each independently represent hydrogen or alkyl having from 1 to 3 carbon atoms, provided that when $n$ is 0 at least one of A, B or C cannot be hydrogen; R represents hydrogen or an alkyl having from 1 to 6 carbon atoms; D and E each independently represent hydrogen or alkyl having from 1 to 6 carbon atoms, provided that the sum of the carbon atoms in D and E does not exceed 6, provided that, in the bicyclo compounds, at least one of A, B, C, D or E must be an alkyl; $m$ is an integer 1 through 8; F and G represent hydrogen or alkyl having from 1 to 3 carbon atoms; X represents

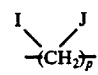

wherein $p$ is an integer 0 through 2 and I and J each independently represent hydrogen or methyl, provided that if $p$ is 0 then $m$ must be greater than 2; provided that the sum of the carbon and oxygen atoms in the compound is no greater than 23, are useful as fragrances or as components in fragrance compositions. These compounds have very pleasant, strong and long-lasting aromas. Novel compounds are also disclosed.

4 Claims, No Drawings

AROMA CHEMICALS

This invention relates to the art of fragrance compositions and, more particularly, to a class of compounds possessing desirable aromas. More specifically, this invention is directed to a class of compounds useful as fragrances or as components in fragrance compositions.

The art of perfumery began, perhaps, in the ancient cave dwellings, of prehistoric man. From its inception, and until comparatively recently, the perfumer has utilized natural perfume chemicals of animal and vegetable origin. Thus, natural perfume chemicals such as the essential oils, for example, oil of rose and oil of cloves, and animal secretions such as musk, have been manipulated by the perfumer to achieve a variety of fragrances. In more recent years, however, research perfume chemists have developed a large number for synthetic odoriferous chemicals possessing aroma characteristics particularly desired in the art. These synthetic aroma chemicals have added a new dimension to the ancient art of the perfumer, since the compounds prepared are usually of a stable chemical nature, are inexpensive as compared with the natural perfume chemicals and lend themselves more easily to manipulation than natural perfume chemicals since such natural perfume chemicals are usually a complex mixture of substances which defy chemical analysis. In contrast thereto, the synthetic aroma chemicals possess a known chemical structure and may therefore be manipulated by the perfumer to suit specific needs. Accordingly, there is a great need in the art of fragrance compositions for compounds possessing specific characteristic aromas.

The principal object of the present invention is to provide such a class of aroma chemicals.

Another object of the present invention is to provide a specific class of compounds having characteristic aromas which are useful in the preparation of fragrances and fragrance compositions.

These and other objects, aspects and advantages of this invention will become apparent from a consideration of the accompanying specification and claims.

In accordance with the above objects, there is provided by the present invention a class of compounds represented by the structural formulae

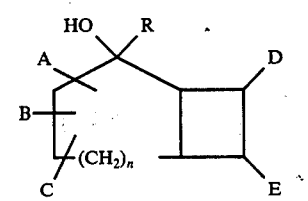 (I)

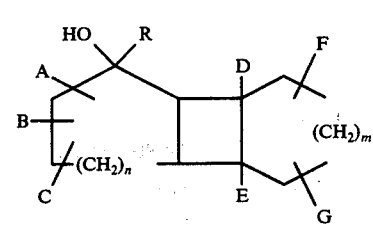 (II)

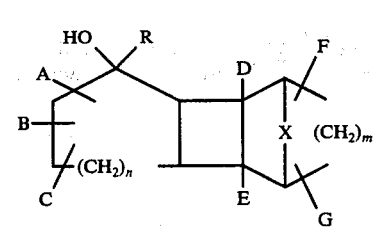 (III)

wherein $n$ is an integer 0 or 1; A, B and C each independently represent hydrogen or alkyl having from 1 to 3 carbon atoms, provided that when $n$ is 0 at least one of A, B or C cannot be hydrogen; R represents hydrogen or alkyl having from 1 to 6 carbon atoms; D and E each independently represent hydrogen or alkyl having from 1 to 6 carbon atoms, provided that the sum of the carbon atoms in D and E does not exceed 6, provided that, in the bicyclo compounds, at least one of A, B, C, D or E must be an alkyl; $m$ is an integer 1 through 8; F and G represent hydrogen or alkyl having from 1 to 3 carbon atoms; X represents

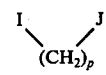

wherein $p$ is an integer 0 through 2 and I and J each independently represent hydrogen or methyl, provided that if p is 0 then $m$ must be greater than 2; provided that the sum of the carbon and oxygen atoms in the compound is no greater than 23. These compounds are useful as fragrances or as components in fragrance compositions.

Synthesis of these compounds can proceed as illustrated in the following equations:

For compounds of Formula I:

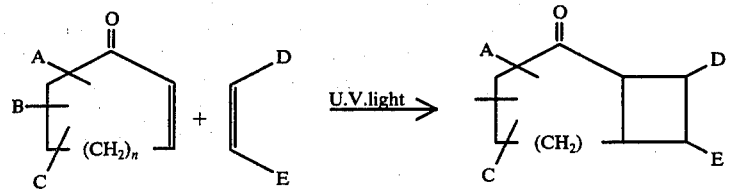

(1)

(2)

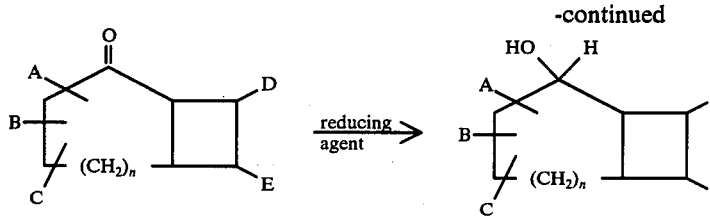

(3)

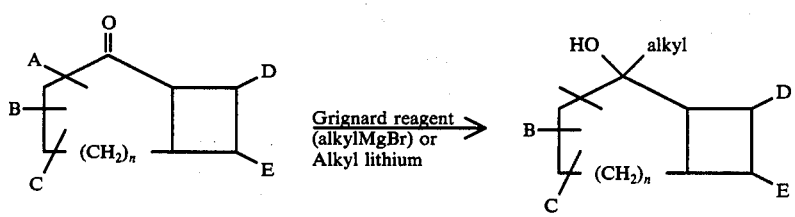

In the above equations, $n$, A, B, C, D and E have the same meanings as set forth above. As shown in equation (1), a substituted or unsubstituted cycloalkenone is reacted with an appropriate substituted or unsubstituted olefin to form the corresponding bicyclo compound. This cycloaddition is readily accomplished by conducting the reaction by irradiation of the reactants in an appropriate solvent through a glass filter which will not pass light having a wave length of less than 2600 A.

As shown in equation (2), the ketone can be reduced to the secondary alcohol (where R is hydrogen) in the presence of a suitable reducing agent such as sodium borohydride, aluminum isopropoxide, or lithium aluminum hydride. As shown in equation (3), the tertiary alcohol (where R is alkyl) can be prepared from the ketone by reaction with a Grignard reagent or an alkyl lithium reagent.

For compounds of Formula II:

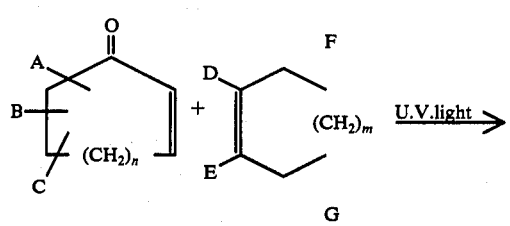

(4)

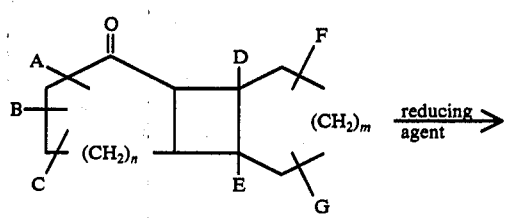

(5)

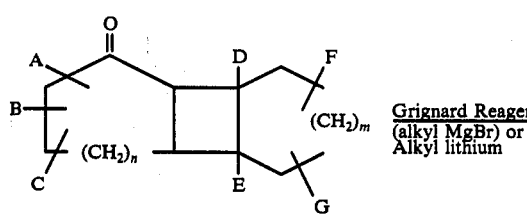

(6)

In the above equations, $n$, A, B, C, D, E, F, G and $m$ have the same meanings as set forth above. As shown in equation (4), the ketone precursors are also formed by a photosynthesis reaction of an appropriate cycloalkenone with an appropriate olefin to obtain the desired cycloaddition compound.

As shown in equation (5), the ketone can be reduced to the secondary alcohol (where R is hydrogen) in the presence of a suitable reducing agent such as sodium borohydride, aluminum isopropoxide, or lithium aluminum hydride. As shown in equation (6), the tertiary alcohol (where R is alkyl) can be prepared from the ketone by reaction with a Grignard reagent or an alkyl lithium reagent.

For compounds of Formula III:

(7)

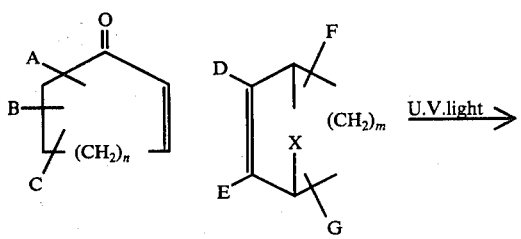

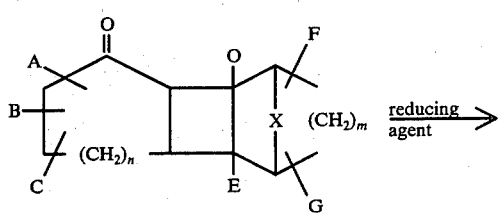

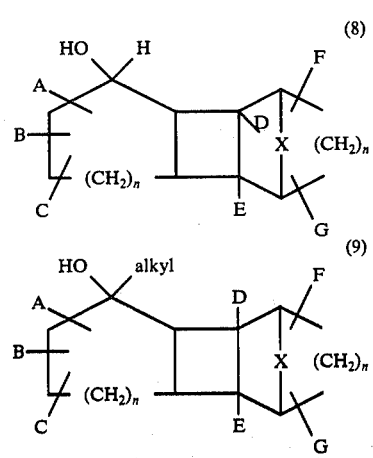

In the above equations, $n$, A, B, C, D, E, F, G, $m$ and X have the same meanings as set forth above. The ketone precursors of the compounds of Formula III can be prepared as shown in equation (7) by a photosynthesis reaction of an appropriate cycloalkenone with an appropriate olefin to obtain the desired cycloaddition compound.

As shown in equation (8), the ketone can be reduced to the secondary alcohol (where R is hydrogen) in the presence of a suitable reducing agent such as sodium borohydride, aluminum isopropoxide, or lithium aluminum hydride. As shown in equation (9), the tertiary alcohol (where R is alkyl) can be prepared from the ketone by reaction with a Grignard reagent or an alkyl lithium reagent.

The reaction conditions for the cycloaddition reaction are not critical but should be such as to facilitate the preparation of the ketones. Thus, the reaction of equations (1), (4) and (7) is normally conducted at a temperature of from low temperatures up to about 150° C. Illustrative solvents useful in these reactions are the olefins themselves, acetonitrile, benzene, acetone, ethyl acetate, hydrocarbons, ethers and methylene chloride. Methylene chloride is a preferred solvent.

The reaction conditions for the formation of the secondary alcohols from the corresponding ketones are not critical but should be such as to facilitate the preparation of the desired alcohols. Thus, the reaction of equations (2), (5) and (8) is normally conducted at a temperature of from ambient up to about 70° C.

Illustrative solvents useful in these reactions are methanol, ethanol and isopropyl alcohol for reactions using sodium borohydride as the reducing agent. For reactions using aluminum isopropoxide as the reducing agent, isopropyl alcohol is the preferred solvent. For reactions using lithium aluminum hydride as the reducing agent, the solvents can be ether or tetrahydrofuran. Tetrahydrofuran is the preferred solvent with this latter reducing agent.

The reaction conditions for the formation of the tertiary alcohols from the corresponding ketones should be carried out at lower temperatures, preferably at or below ambient and in the absence of oxygen and moisture.

Illustrative solvents useful in the reactions of equations (3), (6) and (9) are ether or tetrahydrofuran for the Grignard reagent and ether or hydrocarbon solvents for the alkyl lithium reagent.

More specific details of the procedures for preparation of the ketone precursors of the compounds of the instant invention can be found in copending U.S. patent application Ser. No. 645,188, filed 12-29-75 which is incorporated herein by reference.

More preferred embodiments are those compounds represented by the following structural formula

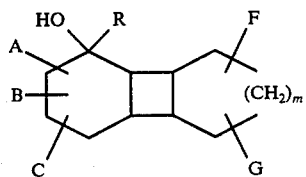

(IV)

wherein A, B, C, F, G, $m$ and R have the same meanings as set forth above.

Still more particularly preferred compounds are represented by the following structural formulae

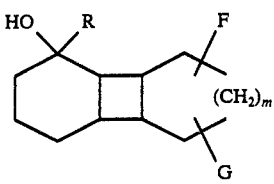

(V)

and (VI)

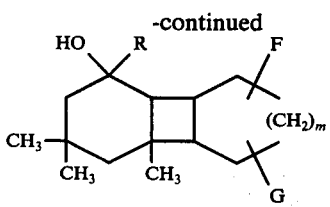

wherein m, F, G and R have the same meanings as set forth above. The compounds of Formula VI are particularly preferred novel compounds.

Compounds which exemplify this invention are
1-methyltricyclo[7.4.0.0$^{2,8}$]tridecane-10-ol
1,10-dimethyltricyclo[7.4.0.0$^{2,8}$]tridecane-10-ol
1,12-dimethyltricyclo[7.4.0.0$^{2,8}$]tridecane-10-ol
1,10,12-trimethyltricyclo[7.4.0.0$^{2,8}$]tridecane-10-ol
1,12,12-trimethyltricyclo[7.4.0.0$^{2,8}$]tridecane-10-ol
1-methyltricyclo[8.4.0.0.$^{2,9}$]tetradecane-11-ol
1-methyl-11-ethyltricyclo-[8.4.0.0$^{2,9}$]tetradecane-11-ol
1,13-dimethyltricyclo[8.4.0.0$^{2,9}$]tetradecane-11-ol
1-methyltricyclo[7.3.0.0$^{2,8}$]dodecane-10-ol
1,10-dimethyltricyclo[7.3.0.0$^{2,8}$]dodecane-10-ol
1,12-dimethyltricyclo[7.3.0.0$^{2,8}$]dodecane-10-ol
1,12,12-trimethyltricyclo[7.3.0.0$^{2,8}$]dodecane-10-ol
7-methyltetracyclo[7.2.2.0$^{2,8}$0$^{3,7}$]tridecane-4-ol
4-(n-hexyl)-7-methyltetracyclo[7.2.2.0$^{2,8}$,0$^{3,7}$]tridecane-4-ol
6,7-dimethyltetracyclo[7.2.2.0$^{2,8}$,0$^{3,7}$]tridecane-4-ol
4-(3-methyl-1-butyl)-6,7-dimethyltetracyclo[7.2.2.0$^{2,8}$,0$^{3,7}$]tridecane-4-ol
6,6,7-trimethyltetracyclo[7.2.2.0$^{2,8}$,0$^{3,7}$]tridecane-4-ol
8-methyltetracyclo[8.2.2.0$^{2,9}$,0$^{3,8}$]tetradecane-4-ol
4,8-dimethyltetracyclo[8.2.2.0$^{2,9}$,0$^{3,8}$]tetradecane-4-ol
6,8-dimethyltetracyclo[8.2.2.0$^{2,9}$,0$^{3,8}$]tetradecane-4-ol
6,6,8-trimethyltetracyclo[8.2.2.0$^{2,9}$0$^{2,8}$]tetradecane-4-ol
7-methyltetracyclo[7.2.1.0$^{2,8}$,0$^{3,7}$]dodecane-4-ol
6,7-dimethyltetracyclo[7.2.1.0$^{2,8}$,0$^{3,7}$]dodecane-4-ol
4,6,7-trimethyltetracyclo[7.2.1.0$^{2,8}$,0$^{3,7}$]dodecane-4-ol
6,6,7-trimethyltetracyclo[7.2.1.0$^{2,8}$,0$^{3,7}$]dodecane-4-ol
4,8,11-(or 12-)trimethyltetracyclo[8.2.1.0$^{2,9}$,0$^{3,8}$]tridecane-4-ol
6,8,11-(or 12-)trimethyltetracyclo[8.2.1.0$^{2,9}$,0$^{3,8}$]tridecane-4-ol
6,6,8,11-(or 12-)tetramethyltetracyclo[8.2.1.0$^{2,9}$,0$^{3,8}$]tridecane-4-ol
1,7,12,12-tetramethyltetracyclo[7.2.1.0$^{2,8}$,0$^{3,7}$]dodecane-4-ol
7,9,12,12-tetramethyltetracyclo[7.2.1.0$^{2,8}$,0$^{3,7}$]dodecane-4-ol
1,6,7,12,12-pentamethyltetracyclo[7.2.1.0$^{2,8}$,0$^{3,7}$]dodecane-4-ol
4,6,7,9,12,12-hexamethyltetracyclo[7.2.1.0$^{2,8}$,0$^{3,7}$]dodecane-4-ol
1,6,6,7,12,12-hexamethyltetracyclo[7.2.1.0$^{2,8}$,0$^{3,7}$]dodecane-4-ol
6,6,7,9,12,12-hexamethyltetracyclo[7.2.1.0$^{2,8}$,0$^{3,7}$]dodecane-4-ol
1,13,13-trimethyltetracyclo[8.2.1.0$^{2,9}$0$^{3,8}$]tridecane-4-ol
4,10,13,13-tetramethyltetracyclo[8.2.1.0$^{2,9}$0$^{3,8}$]tridecane-4-ol
1,8,13,13-tetramethyltetracyclo[8.2.1.0$^{2,9}$0$^{3,9}$]tridecane-4-ol
8,10,13,13-tetramethyltetracyclo[8.2.1.0$^{2,9}$0$^{3,8}$]tridecane-4-ol
1,6,8,13,13-pentamethyltetracyclo[8.2.1.0$^{2,9}$0$^{3,8}$]tridecane-4-ol
6,8,10,13,13-pentamethyltetracyclo[8.2.1.0$^{2,9}$0$^{3,8}$]-tridecane4-ol
1,6,6,8,13,13-hexamethyltetracyclo[8.2.1.0$^{2,9}$0$^{3,8}$]tridecane-4-ol
6,6,8,10,13,13-hexamethyltetracyclo[8.2.1.0$^{2,9}$0$^{3,8}$]tridecane-4-ol
4-(or 5-)t-butyl-1-methyltricyclo[6.3.0.0$^{2,7}$]undecane-9-ol
4-(or 5-)t-butyl-1,9-dimethyltricyclo[6.3.0.0.$^{2,7}$]undecane-9-ol
4-(or 5-)t-butyl-1,11,11-trimethyltricyclo[6.3.0.0$^{2,7}$]undecane-9-ol
10-(or 11-)t-butyltricyclo[6.4.0.0$^{2,7}$]dodecane-3-ol
10-(or 11-)t-butyl-7-methyltricyclo[6.4.0.0$^{2,7}$]dodecane-3-ol
10-(or 11-)t-butyl-3,7-dimethyltricyclo[6.4.0.0$^{2,7}$]dodecane-3-ol
10-(or 11-)t-butyl-5,5,7-trimethyltricyclo[6.4.0.0$^{2,7}$]dodecane-3-ol
7-t-butyl-5-methylbicyclo[3.2.0]heptane-2-ol
7-t-butyl-2,4,5-trimethylbicyclo[3.2.0]heptane-2-ol
7-t-butyl-4,4,5-trimethylbicyclo[3.2.0]heptane-2-ol
1-methyltricyclo[9.3.0.0$^{2,10}$]tetradecane-12-ol
1-methyl-12-n-propyltricyclo[9.2.0.0$^{2,10}$]tetradecane-12-ol
1,14-dimethyltricyclo[9.3.0.0$^{2,10}$]tetradecane-12-ol
1,14,14-trimethyltricyclo[9.3.0.0$^{2,10}$]tetradecane-12-ol
1-methyltricyclo[10.3.0.0$^{2,11}$]pentadecane-13-ol
1,15-dimethyltricyclo[10.3.0.0$^{2,11}$]pentadecane-13-ol
1,13,15-trimethyltricyclo[10.3.0.0$^{2,11}$]pentadecane-13-ol
tricyclo]9.4.0.0$^{2,10}$]pentadecane-12-ol
1-methyltricyclo[9.4.0.0$^{2,10}$]pentadecane-12-ol
1,14-dimethyltricyclo[9.4.0.0$^{2,10}$]pentadecane-12-ol
1,12,14-trimethyltricyclo[9.4.0.0$^{2,10}$]pentadecane-12-ol
tricyclo[10.4.0.0$^{2,11}$]hexadecane-13-ol
1-methyltricyclo[10.4.0.0$^{2,11}$]hexadecane-13-ol
1,15-dimethyltricyclo[10.4.0.0$^{2,11}$]hexadecane-13-ol
1,13,15-trimethyltricyclo[10.4.0.0$^{2,11}$]hexadecane-13-ol
tricyclo[6.3.0.0$^{2,7}$]undecane-3-ol
7-methyltricyclo[6.3.0.0$^{2,7}$]undecane-3-ol
5,7-dimethyltricyclo[6.3.0.0$^{2,7}$]undecane-3-ol
3,5,7-trimethyltricyclo[6.3.0.0$^{2,7}$]undecane-3-ol
6-methyltricyclo[5.3.0.0$^{2,6}$]decane-3-ol
5,6-dimethyltricyclo[5.3.0.0$^{2,6}$]decane-3-ol
3,5,6-trimethyltricyclo[5.3.0.0$^{2,6decane}$]-3-ol   1-methyltricyclo[6.3.0.0$^{2,7}$]undecane-9-ol
1,11-dimethyltricyclo[6.3.0.0$^{2,7}$]undecane-9-ol
1,9,11-trimethyltricyclo[6.3.0.0$^{2,7}$]undecane-9-ol
6-(or 7-)n-hexy-5-methylbicyclo[3.2.0]heptane-2-ol
6-(or 7-)n-hexyl-4,5-dimethylbicyclo[3.2.0]heptane-2-ol
6-(or 7-)n-hexyl-2,4,5-trimethylbicyclo[3.2.0]heptane-2-ol
7-(or 8-)n-hexylbicyclo[4.2.0]octane-2-ol
7-(or 8-)n-hexyl-6-methylbicyclo[4.2.0]octane-2-ol
7-(or 8-)n-hexyl-4,6-dimethylbicyclo[4.2.0]octane-2-ol
7-(or 8-)n-hexyl-2,4,6-trimethylbicyclo[4.2.0]octane-2-ol The compounds of this invention are useful as fragrances in the preparation and formulation of fragrance compositions such as perfumes and perfumed products due to their pleasing, strong and long-lasting aroma. Perfume compositions and the use thereof in cosmetic, detergent and bar soap formulations and the like are exemplary of the utility thereof. Likewise, these compounds can be utilized as the primary fragrance in many such compositions.

It has been determined that the structural formulae of the compounds of this invention form many different spatial configurations, i.e., mixtures of stereo isomers. These mixtures of isomers all appear to exhibit fragrance characteristics that are desired by perfumers in compounding fragrances.

The compounds of this invention are used in concentrations of from trace amounts up to about 50 percent of the fragrance composition into which they are incorporated. As will be expected, the concentration of the compound will vary depending on the particular fragrance desired in the composition and even within the same composition when compounded by different perfumers.

It has been found that the compounds of this invention possess notes with good intensity and persistence. This fragrance quality particularly adapts the compounds for incorporation into fragrance compositions and fragrance modifying compositions having a desirable aroma. It will be appreciated by those skilled in the art from the present invention that the fragrance character of the finished fragrance compositions can be tailored to specific uses, as more fully described hereinafter.

The compounds of this invention are olfactory agents and can be incorporated into a wide variety of compositions which will be enhanced by their fragrance notes. The compounds can be added to fragrance compositions in pure form or they can be added to mixtures of materials in fragrance-imparting compositions to provide a desired fragrance character to a finished fragrance material. The fragrance compositions obtained according to this invention are suitable in a wide variety of perfumed articles and can also be used to enhance, modify or reinforce natural fragrance materials. It will thus be appreciated that the compounds of this invention are useful as olfactory agents and fragrances.

The term "fragrance composition" is used herein to means a mixture of compounds, including, for example, natural oils, synthetic oils, alcohols, aldehydes, ketones, esters, lactones, and frequently hydrocarbons which are admixed so that the combined odors of the individual components produce a pleasant or desired fragrance. Such fragrance compositions usually contain (a) the main note or the "bouquet" or foundationstone of the composition; (b) modifiers which round off and accompany the main note; (c) fixatives which include odorous substances which lend a particular note to the fragrance throughout all stages of evaporation, and substances which retard evaporation; and (d) top-notes which are usually low-boiling, fresh-smelling materials. Such fragrance compositions of this invention can be used in conjunction with carriers, vehicles, solvents, dispersants, emulsifiers, surface-active agents, aerosol propellants, and the like.

In fragrance compositions the individual components contribute their particular olfactory characteristics, but the overall effect of the fragrance composition will be the sum of the effect of each component. Thus, the compounds of this invention can be used to alter the aroma characteristics of a fragrance composition, for example, by highlighting or moderating the olfactory reaction contributed by another component of the composition.

The amount of compounds of this invention which will be effective in fragrance compositions depends on many factors, including the other components, their amounts and the effects which are desired. It has been found that fragrance compositions containing as much as 50% by weight or as little as trace amounts of mixtures of compounds of this invention, or even less, can be used to impart a desirable odor to soaps, cosmetics and other products. The amount employed will depend on considerations of cost, nature of the end product, the effect desired in the finished product, and the particular fragrance sought.

The compounds disclosed herein can be used alone, in a fragrance-modifying composition, or in a fragrance composition as an olfactory component in detergents and soaps; space deodorants; perfumes; colognes; bath preparations such as bath oil, bath salts, hair preparations such as lacquers, brilliantines, pomades, and shampoos; cosmetic preparations such as creams, deodorants, hand lotions, sun screens; powders such as talcs, dusting powders, face powder and the like. When the compounds of this invention are used in perfumed articles such as the foregoing, it can be used in amounts of 0.1% or lower. Generally, it is preferred not to use more than about 10% in the finished perfumed article, since the use of too much will tend to unbalance the total aroma and will needlessly raise the cost of the article.

The following Examples will serve to illustrate certain specific embodiments within the scope of this invention and are not to be construed as limiting the scope thereof.

EXAMPLE I 4,4,6-trimethylbicyclo[4.2.0]octane-2-ol

To a 2-liter 3-necked flask fitted with a mechanical stirrer, additional funnel, reflux condenser and drying tube was added 15 g. (0.39 mole) of sodium borohydride and 500 ml. 2-propanol. To this solution was slowly added 218.6 g. (1.317 moles) of 4,4,6-trimethylbicyclo[4.2.0]octane-2-one in 50 ml. of 2-propanol. After 2 hours, about 200 ml. of water was added. The mixture was stirred an additional 1 hour, then about 35 ml. concentrated hydrochloric acid was added. After another 1 hour of stirring, 400 ml. of toluene and 500 ml. of water were added. The layers were separated and the organic layer was washed three times with 100 ml. of water. The combined water layers were extracted with toluene. The toluene layers were combined and dried over potassium carbonate. The solution was concentrated in vacuo and the residue distilled through a 25 cm. Vigreux--column to yield 215.8 g. (1.284 moles, 97.5% yield) of 4,4,6-trimethylbicyclo [4.2.0]octane-2-ol. IR: 3360 cm$^{-1}$.

EXAMPLE II tricyclo[8.4.0.0$^{2,9}$]tetradecane-11-ol

To a solution of 2.06 g. (0.01 mole) of the tricyclo ketone in 100 ml. of 2-propanol in a 250 ml. Erlenmeyer flask equipped with magnetic stirring bar was added 0.57 g. (0.015 mole) of sodium borohydride. The reaction mixture was stirred overnight. The mixture was transferred to a separatory funnel, a few drops of concentrated hydrochloric acid added, and then extracted with three 100 ml. portions of ether. The combined ether extracts were washed with three 25 ml. portions of 10% aqueous sodium bicarbonate solution, dried over magnesium sulfate and concentrated in vacuo to yield a white crystalline solid that was recrystallized from petroleum ether to yield 1.20 g. (0.0058 mole, 58% yield) of tricyclo[8.4.0.0$^{2,9}$]tetradecane-11-ol. m.p.: 141.5°–142.0° C. IR: 3610 cm$^{-1}$, 3450 cm$^{-1}$.

EXAMPLE III

5,5,7-trimethyltricyclo[6.4.0.0$^{2,7}$]dodecane-3-ol

To 7.0 g. (0.19 mole) of sodium borohydride in 400 ml. of isopropyl alcohol in a 1-liter round bottomed flask equipped with magnetic stirrer, reflux condenser and drying tube is added 140 g. (0.636 mole) of 5,5,7-trimethyltricyclo [6.4.0.0$^{3,7}$]dodecane-3-one in 100 ml. of isopropyl alcohol. The mixture is stirred for about 15 hours and then 300 ml. of a saturated aqueous sodium chloride solution containing 70 ml. of concentrated hydrochloric acid is cautiously added. The entire mixture is transferred to a 1-liter separatory funnel and the layers are separated. The aqueous layer is extracted three times with 100 ml. of petroleum ether. The organic layers are combined, extracted three times with 100 ml. of water, dried over magnesium sulfate and concentrated in vacuo to yield the product as a viscous oil. 127.5 g. of 5,5,7-trimethyltricyclo[6.4.0.0$^{2,7}$]dodecane-3-ol was recovered (0.572 mol., 90% yield). IR: 3380 cm$^{-1}$, b.p. 104-110° C./0.2 mm.

EXAMPLE IV

2,4,4,6-tetramethylbicyclo[4.2.0]octane-2-ol

To 0.97 g. (0.04 g. atom) of magnesium in a 250 ml. 3-necked round bottomed flask fitted with dropping funnel, magnetic stirrer, and nitrogen inlet was added 25 ml. of ether. Then 5.0 g. (0.035 mole) of methyl iodide in 100 ml. of ether was added from a dropping funnel at such a rate that reflux was maintained as the Grignard reagent was formed. After all the methyl iodide was added, the solution was stirred and refluxed for an additional 1 hour. Then 4.98 g. (0.03 mole) of 4,4,6-trimethylbicyclo[4.2.0]octane-2-one was added in 75 ml. of ether over 30 minutes. After all of the ketone was added, the solution was stirred for an additional 1 hour and then 50 ml. of saturated aqueous ammonium chloride was added. The layers were separated and the aqueous layer was extracted twice with 50 ml. portions of ether. The combined ether layers were dried over sodium sulfate and concentrated in vacuo to yield a solid which was sublimed. The recovered product was 5.3 g. (0.029 mole, 97% yield) of 2,4,4,6-tetramethylbicyclo[4.2.0]octane-2-ol. m.p. 54° - 55° C. nmr: (deuterochloroform): 0.92$\delta$ (S-34); 1.02$\delta$ (S-34); 1.13$\delta$ (S-34); 1.21$\delta$ (S-34); 1.28$\delta$ - 2.25$\delta$ (complex multiplets 10H). IR: 3610 cm$^{-1}$.

EXAMPLE V

3,5,5,7-tetramethyltricyclo[6.4.0.0$^{2,7}$]dodecane-3-ol

To a photoreactor fitted with a quartz immersion well and nitrogen bubbler was added, under nitrogen, 30.0 g. (0.217 mole) of isophorone and 145 ml. of freshly distilled cyclohexene. Enough dichloromethane was added to fill the 825 ml. internal volume of the photoreactor. After the solution was bubbled with nitrogen for 1 hour, it was irradiated through a Corning 9700 glass filter for 7¼ hours with an Hanovia 450 watt medium pressure mercury arc. At the end of this period, the solution was concentrated in vacuo to yield an oil which was distilled through a short Vigreux-column. The product, which is 5,5,7-trimethyltricyclo[6.4.0.0$^{2,7}$]dodecane-3-one, which is a mixture of two major isomers in approximately a 3:1 ratio had b.p. 93°-106° c./0.2 mm. Hg. Yield: 39.2 g. (0.178 mole, 82% yield). These two isomers could be separated by distillation on a spinning band column. Isomer A: b.p. 85° C./0.1 mm. Hg. m.p. 76.6°-77.4° C., IR: 1690 cm$^{-1}$; nmr: deuterochloroform 1.20$\delta$ (S-3H); 1.07$\delta$ (S-3H); 0.90$\delta$ (S-3H); 1.32$\delta$-2.70$\delta$ (complex multiplets 15H). Isomer B: b.p. 95° C./0.1 Hg. IR: 1690 cm$^{-1}$, nmr: deuterochloroform; 1.08$\delta$, 1.05$\delta$ (2singlets-6H); 0.90$\delta$ (S-3H) 1.18$\delta$- 2.83$\delta$ (multiplets 15H).

ISOMER A

In a 2-liter, 3-necked flask fitted with a tantalum wire Hershberg stirrer, condenser, dropping funnel, and under nitrogen, is placed 26.7 g. (1.1 moles) Grignard quality magnesium chips and 10 - 15 moles of ether. Several drops of methyl iodide is added. When the solution becomes cloudy, the remainder of 163 g. (1.15 moles) of methyl iodide in about 600 ml. of ether was added at a rate sufficient to maintain gentle reflux. The mixture was stirred for an additional 0.5 hour and then 220 g. (1.0 mole) of Isomer A of 5,5,7-trimethyltricyclo[6.4.0.0$^{2,7}$]dodecane-3-one was added over 0.5 hour. The reaction mixture was stirred overnight and then decomposed by the cautious addition of about 160 ml. of saturated aqueous ammonium chloride solution. The ether layer was decanted and the precipitated solid was thoroughly washed with benzene. The combined organic solutions were evaporated to leave a yellow, sticky solid, 228.6 g. (96.9% yield). The solid was dissolved to form a petroleum ether solution which was treated with charcoal and filtered to give a slightly yellow solution from which large crystals gradually separated as the solvent slowly evaporated. From time to time batches of crystals were filtered from the solution and washed with fresh petroleum ether. The filtrate and washings on standing gave additional material until finally 200 g. of product, 3,5,5,7-tetramethyltricyclo[6.4.0.0$^{2,7}$]dodecane-3-ol, (Isomer A) which is itself a mixture of isomers, was collected. The material begins to shrink and soften at 57° C., with liquid clearly apparent near 72° C. and complete melting at 85.5° C. IR: 3605 cm$^{-1}$.

ISOMER B

Using Isomer B (ketone), a procedure similar to that set forth in Example IV is followed to prepare the tertiary alcohol, 3,5,5.7-tetramethyltricyclo[6.4.0.0$^{2,7}$]dodecane-4-ol (Isomer B) in 78% yield. nmr: carbon tetrachloride 0.88$\delta$ (S-3H); 0.99$\delta$ (S-3H); 1.08$\delta$ (S-3H); 1.13$\delta$ (S-3H) and about 1.23$\delta$-2.3$\delta$ (multiplets - 16H). IR: 3610 cm$^{-1}$.

EXAMPLE VI

A fragrance composition illustrative of the instant invention contains the following components:

| Component | Parts by Weight |
|---|---|
| Coumarin | 9.0 |
| Compound of Example V(A) | 6.0 |
| Bergamot Oil | 33.0 |
| Castoreum Extract (5% in dipropylene glycol) | 16.0 |
| Lavander Oil | 1.5 |
| Lemon Oil | 10.0 |
| Myrrh Extract (50% in dipropylene glycol) | 1.5 |
| Orange Oil | 11.5 |
| Opoponax Extract (50% in dipropylene glycol) | 6.0 |
| Patchouly Oil | 1.0 |
| Citronellol Oil | 3.0 |
| Sandalwood Oil | 1.5 |

This fragrance composition imparts a pleasant, sweet, powdery, woody aroma.

EXAMPLE VII

The characteristic aromas of some of the compounds of the instant invention are as follows:

| Compound of Example | Aroma |
| --- | --- |
| I | camphor, minty, woody, patchouly |
| II | weak to odorless, woody |
| III | sandalwood |
| IV | camphoraceous, musty, sweet (extremely) |
| VI | sweet, powdery, weak, fairly lasting |

While the invention has been described herein with regard to certain specific embodiments, it is not so limited. It is to be understood that variations and modifications thereof may be made by those skilled in the art without departing from the spirit and scope of the invention.

The embodiments of this invention in which a particular property or privilege is claimed are defined as follows:

1. A compound represented by the structural formula

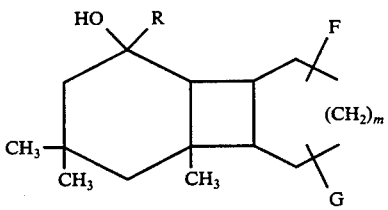

wherein $m$ is an integer from 1 through 8; F and G represent hydrogen or alkyl having from 1 to 3 carbon atoms; and R represents hydrogen or an alkyl having from 1 to 6 carbon atoms.

2. A compound according to claim 1 wherein $m$ is 2.

3. A compound according to claim 2 which is 3,5,5,7-tetramethyltricyclo[6.4.0.0$^{2,7}$]dodecane-3-ol.

4. A compound according to claim 3 which is 5,5,7-trimethyltricylco[6.4.0.0$^{2,7}$]dodecane-3-ol.

* * * * *

UNITED STATES PATENT OFFICE
CERTIFICATE OF CORRECTION

PATENT NO. : 4,044,057
DATED : August 23, 1977
INVENTOR(S) : Jordan J. Bloomfield and Dennis C. Owsley It is certified that error appears in the above-identified patent and that said Letters Patent are hereby corrected as shown below:

Column 6, first formula, should be corrected to read
"

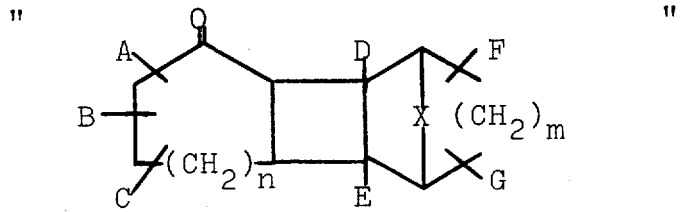

"

Formula (8), bridging columns 5 and 6, should be corrected to read

"

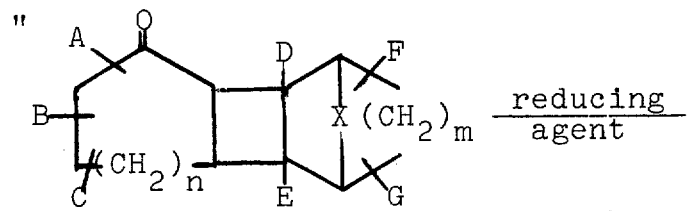

"

Column 7, line 63, "$[8.2.1.0^{2,9}0^{3,9}]$" should be corrected to read -- $[8.2.1.0^{2,9}0^{3,8}]$ --.

Column 8, line 24, "$[9.2.0.0^{2,10}]$" should be corrected to read -- $[9.3.0.0^{2,10}]$ --.

Column 8, line 45, "1-methyl-" should be deleted and inserted in line 46.

Column 8, line 49, "hexy" should be corrected to read -- hexyl --.

Column 12, line 46, "4" should be corrected to read -- 3 --.

UNITED STATES PATENT OFFICE
CERTIFICATE OF CORRECTION

PATENT NO. : 4,044,057
DATED : August 23, 1977
INVENTOR(S) : Jordan J. Bloomfield and Dennis C. Owsley It is certified that error appears in the above-identified patent and that said Letters Patent are hereby corrected as shown below:

Column 13, line 1 of the table, "i" should be corrected to read "I".

Column 14, line 24, "trimethyltricylco" should be corrected to read -- trimethyltricyclo --.

Signed and Sealed this

Seventh Day of February 1978

[SEAL]

Attest:

RUTH C. MASON
Attesting Officer

LUTRELLE F. PARKER
Acting Commissioner of Patents and Trademarks